Figure 1A:
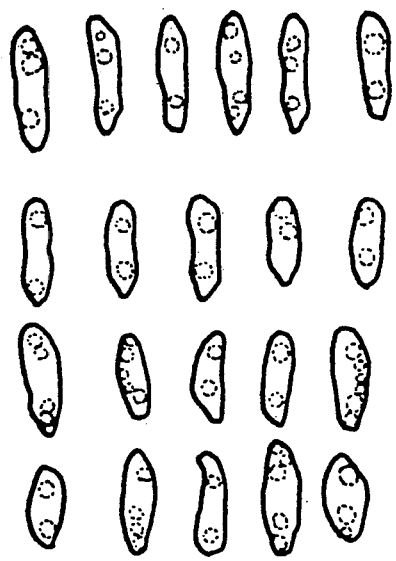

United States Patent [19]

Leth

[11] Patent Number: 4,753,670

[45] Date of Patent: Jun. 28, 1988

[54] HERBICIDE

[75] Inventor: Vibeke Leth, Skaevinge, Denmark

[73] Assignee: Novo Industri A/S, Bagsvaerd, Denmark

[21] Appl. No.: 647,609

[22] Filed: Sep. 6, 1984

[30] Foreign Application Priority Data

Sep. 7, 1983 [DK] Denmark ............................ 4059/83

[51] Int. Cl.[4] ........................................... A01N 63/04
[52] U.S. Cl. ....................................... 71/79; 435/911
[58] Field of Search ............................ 71/79; 435/911

[56] References Cited

U.S. PATENT DOCUMENTS 3,347,909 10/1967 Lowe et al. ............................ 71/113
3,999,973 12/1976 Templeton ............................. 71/79
4,390,360 6/1983 Walker ................................... 71/79

OTHER PUBLICATIONS

Cole et al, "Isolation and Biological, etc.," (1981) CA 94:61234s (1981).
Cutler et al, "Fungal Metabolites, etc.," (1979) CA 92:141619v (1980).
Sharp et al, "Biological Control of Weeds, etc.," Federal Research in Progress, ID No. 0046477 (6-1983 or 3-1985).
Yu, "Septoria Leaf Spot of Plants, etc.," Liet. Tsr. Mokslu Akad. Darb Ser C Biol Mokslai, pp. 57-74 (1980).
Peresypkin et al, "Effect of Septoria, etc.," (1977) CA 89:160317z (1978).
R. Charudattan et al, "Biological Control of Weeds, etc.," 1982, pp. 62-63.

Primary Examiner—Glennon H. Hollrah
Assistant Examiner—Patricia L. Morris
Attorney, Agent, or Firm—Morris Fidelman; Franklin D. Wolffe

[57] ABSTRACT

Disease causing material obtained by cultivation of *Phomopsis cirsii* or *Septoria cirsii* can be used for controlling weeds such as compositae.

6 Claims, 2 Drawing Sheets

10 μm

HERBICIDE

This invention relates to a mycoherbicidal composition comprising an effective amount of the disease causing material obtained by cultivation of *Phomopsis cirsii* or *Septoria cirsii*, optionally containing other active materials and an agronomically compatible diluent or carrier and the use of the herbicidal composition against plants belonging to the composites (Compositae). Preferably, *Phomopsis cirsii* is used.

The fungi are propagated on nutritive substrates after which the fresh or preserved disease causing material obtained is spread in suitable amounts over the weeds in the field.

BACKGROUND OF THE INVENTION

Other artificially propagated sorts of fungi which are used in a similar way against other types of weeds, are known (see Weed Science 21 (1973), 303 et seq., Ann. Rev. Phytopathol. 17 (1979), 301 et seq., and Plant Disease Reporter 58 (1974), 355 et seq.) and these so-called mycoherbicides are sold to-day under the trademarks Devine TM and Collego TM (Phytopathology 73 (1983), 774).

As of the date hereof, weeds belonging to the Compositae are controlled with chemical herbicides. These often have little effect on the weeds, which fact may be due to unfavourable climatic conditions at the time of spraying or to the fact that use of the known herbicides over an extended period of time selects for herbicide tolerant types of weeds. For these reasons and for environmental reasons it is desirable to use biological herbicides.

The fungus *Phomopsis cirsii* Grove was described for the first time by Grove in British Stem- and Leaf-fungi (Coelomycetes) 1 (1935), 177, and the fungus *Septoria cirsii* Niessl was described by Saccardo in Sylloge Fungorum 3 (1884), 550.

The pathogenic effects of *Phomopsis cirsii* and of *Septoria cirsii* on plants have so far been unknown. Surprisingly, it has now been found that *Phomopsis cirsii* attacks the leaf veins and stems of the host plants which as the disease progresses will shrink and wither. Such symptoms can be traced to the formation of toxins in the plant. The secretion of specific phytotoxic substances from the fungus or from interaction between the plant and fungus can also be seen in that parts of the infected plant, which show no signs of invasion by the fungus, turn yellow and wither earlier than they would normally have done. This means that phytotoxic products elaborated by the fungus have a controlling effect on the host plants.

BRIEF STATEMENT OF THE INVENTION

Plants may be controlled by spraying with a disease causing material or materials obtained by cultivation of *Phomopsis cirsii* such as fragments of mycelium, sclerotia, pycnidia, conidia and phytotoxic products therefrom.

Plants may be infected by spraying with a disease causing material obtained by cultivation of *Septoria cirsii* such as pycnidia, conidia and phytotoxic products therefrom.

Each of these fungal structures can be used alone or together as disease causing material. The disease causing material may also be obtained from different strains of the fungi.

In the herbicidal composition of this invention the disease causing material obtained by cultivation of either *Phomopsis cirsii* or *Septoria cirsii* can be used separately, but if disease causing material obtained from both fungi is used, a wider range of host plants and a higher ecological amplitude is obtained. This will, all things considered, have the most appropriate controlling effect.

DISCUSSION OF THE INVENTION

It has not previously been known that it is possible to prepare a disease causing material by cultivation of *Phomopsis cirsii* or *Septoria cirsii*, and that such material can be used as plant growth-inhibiting agent or as herbicide. Furthermore, the specificity of the disease causing material described herein against different plant species is surprising.

Immature pycnidia from *Phomopsis cirsii* are glabrous, lenticular and covered by the epidermis. Later, under moist conditions, the pycnidia produce long prominent necks which penetrate the epidermis. Mature pycnidia are pyriform, unilocular, at basis broad to flattened and thin-walled. Wall thickness increases towards the neck. The cavity is mostly simple but sometimes (predominantly in dry material) divided by intrusions from the inner wall.

There are some inconsistencies between the morphology of the pycnidia from *Phomopsis cirsii* on the plant and in culture, but the succession of conidia types produced on the plant and the characteristics of the conidia are identical to the characteristics of the fungus in culture (described hereinafter).

Colonies of *Phomopsis cirsii*, cultivated from mycelium isolated from infected plants of *Cirsium arvense*, are fast growing on 2% Potato Dextrose Agar (hereinafter: PDA) reaching about 9 cm in diameter after 3 days at 20° C. On PDA added 1 g of Novobiocin per liter substrate, the growth is strongly inhibited and ceases at about 2 cm in diameter, leaving a lemon yellow zone (halo) of discoloured medium.

In general (on 2% PDA), colonies on PDA exhibit a certain variation in colour during the aging of the culture. Initially, they are whitish, transitionally often with greenish yellow mycelium in patches or in a zone extending up to 2 cm from the periphery towards the center of the colony. Later the colonies become greyish brown. The surface is floccose. The margin initially with abundant aerial mycelium, with age becoming appressed. Old cultures may produce raised circular tufts of dense white mycelium, about 3 to 5 mm in diameter.

Reverse initially colourless or beige, transitionally with brown patches. Finally, the culture is light brown, chestnut brown or black.

In cultures originating from pieces of mycelium, pycnidia develop imbedded in the PDA after about 35 to 40 days at room temperature.

During the early stages, the pycnidia are solitary, relatively small, thin-walled and dark brown to black. With the process of aging, larger and more thick-walled pycnidia develop either in clusters (groups) or in complexes with interconnected walls often sharing one ostiole only.

Under humid conditions, predominantly pronounced elongated simple or branched necks with apicale ostioles are formed from which conidia are extruded in opaque globules. On PDA plates, colonies derived from these conidia (globules) resembled those from mycelium. Using conidia, pycnidium formation occured after about 14 to 20 days.

Figure 1B:
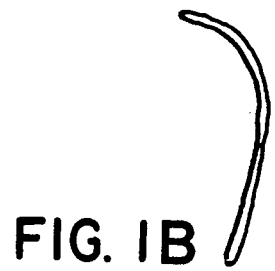
Figure 1C:
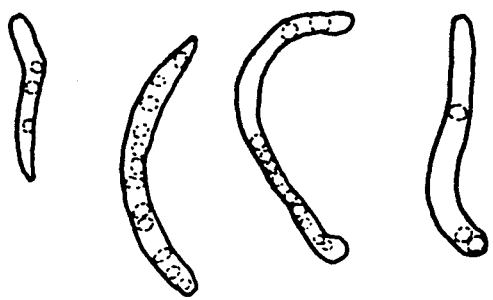
Figure 2:
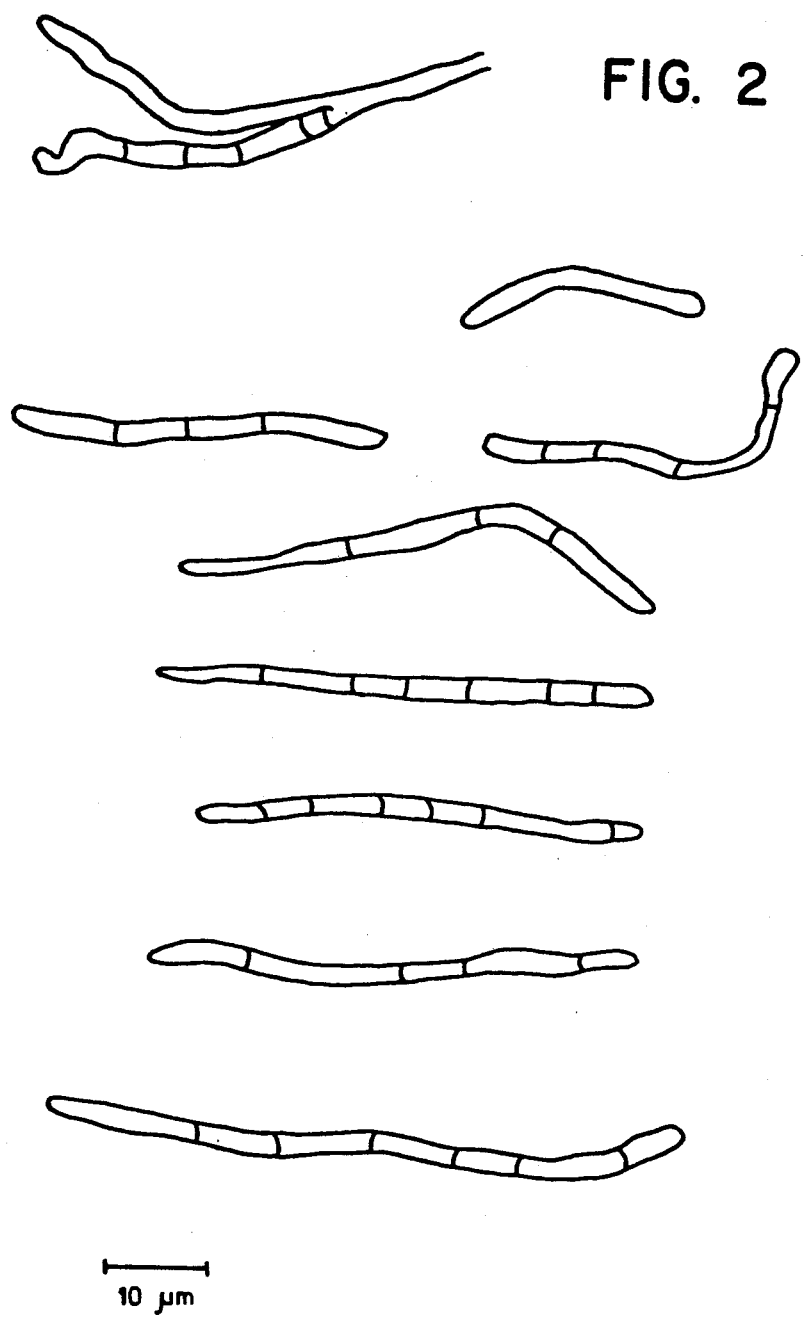

For further understanding of the fungi employed in practice of this invention reference is made to the attached drawing wherein:

FIG. 1 shows typical conidia of *Phomopsis cirsii;* and
FIG. 2 shows typical conidia of *Septoria cirsii.*

As most Phomopsis species, *Phomopsis cirsii* is capable of producing three types of conidia. On the plants as well as in culture, the type of conidia varies as a result of the pycnidium age (see FIG. 1 showing A-, B-, and C-conidia). B-conidia are typically the first conidia to be produced. Later in the same pycnidium A-conidia are formed and gradually become more abundant. When A-conidia occur, the C-conidia, which are an intermediary type between A- and B-conidia, can be found in small numbers. The dimensions of the conidia seem to depend on the substrate on which the fungus has been cultivated. The following descriptions of conidia are, however, based upon observations and measurements made on conidia collected from plants and from cultures on PDA, on V8 agar and on oat meal agar.

The A-conidia are hyaline, unicellular, guttulate and ellipsoid, often slightly constricted in the mid region; measuring about 7–10×2–3 $\mu$m. The B-conidia are hyaline, usually curved at one end or flexuos; measuring about 18–35×0.5–1 $\mu$m. The C-conidia are hyaline, slightly curved with round or acute ends sometimes ellipsoid, resembling long A-conidia but mostly multi guttulate; measuring about 14–30×2.5–3 $\mu$m.

On PDA plates at room temperature, deviations in growth characters, in willingness in formation of pycnidia and in the succession in which A- and B-conidia are produced were found among different strains of *Phomopsis cirsii.*

Two out of 15 strains of *Phomopsis cirsii* produced granular, appressed, white mycelium with very few solitary pycnidia. Another strain, though displaying typical colony characteristics, produced A-conidia before B-conidia.

Several species of Phompsis are the conidial stage of the genus Diaporthe Nits. in the class of Pyrenomycetes in Ascomycotina. No ascocarps or any other sexual structure have been observed on the cultures of *Phomopsis cirsii,* even when they were kept for one year at room temperature, at 4° C. or at alternating conditions in laboratory or in nature.

Pycnidia from *Septoria cirsii* are single and immersed, the shape is globose or depressed globose with a diameter of about 40–100 $\mu$m, without papilla or neck. The conidia producing layer is lining the entire inner surface of the cavity. The pycnidial wall is stromatic, composed of several layers of heavily pigmented and relatively thick walled cells.

Conidia (about 20–80×2–3 $\mu$m) are cylindrical, subflexous and normally with 6–12 septa. One end truncate to rounded, the other end narrowed and more acute. Sometimes conidia are without any signs of septation or with only five or fewer distinct septa, all within the same pycnidia (see FIG. 2 showing conidia of *Septoria cirsii* from culture on PDA).

*Septoria cirsii* grows well on liquid as well as on solid PDA, but not on Czapek Dox Broth (Difco Laboratories, Detroit, USA). On PDA plates, colonies derived from mycelium grows very slowly, producing white, sometimes silvery raised hairy colonies with smooth margins, reaching about 4 cm in diameter after one month of incubation at room temperature with or without NUV-light. Only very few or no pycnidia are produced in this colony type. Colonies derived from conidia immediately produce pycnidia immersed in the medium with a minimal mycelium. After about 7 days of incubation at room temperature, mature pycnidia are formed with conidia extruded in opaque or very seldom in rose-pink globules from the ostioles.

The shape of the pycnidia and conidia and their dimensions in culture are in accordance with the characteristics of the fungus on *Cirsium arvense.*

According to Oudemans: Enumeratio Systematica Fungorum 4 (1923), 1073 et seq., *Septoria cirsii* has previously been found on Cirsium sp., on *Cirsium arvense* (L.) Scop., on *Carthamus lanatus* L. (*Kentrophyllum lanatum* D.C.) and on *Seratula glauca* Ledeb. According to page 43 in Bulletin 414 from Ohio Agricultural Experimental Station 1927, *Septoria cirsii* does not seriously injure *Cirsium arvense* and, therefore, the utility of the fungus for herbicidal compositions is surprising.

*Phomopsis cirsii* and *Septoria cirsii* can be cultivated by surface cultivation or by submerged cultivation.

Surface cultivation is carried out on a liquid medium containing an assimilable nitrogen and carbon source and essential nutrients.

Submerged cultivation is carried out under aerobic conditions in a fermentation medium comprising an assimilable nitrogen, carbon source and essential nutrients whereafter the disease causing material is isolated. Further details such as pH value, temperature, aeration and agitation can easily be selected by the skilled art worker.

In 1983, a strain of *Phomopsis cirsii* was deposited at the Commonwealth Mycological Institute Culture Collection (CMI), Ferry Lane, Kew, United Kingdom, under the herbarium No. 278,416. In 1983, a strain of *Septoria cirsii* was deposited at the CMI under No. 280,201. On 17 July 1984, 4 further strains of *Phomopsis cirsii* were deposited at the CMI under the Nos. 287,566 through 287,569 and on 27 July 1984, 2 further strains of *Septoria cirsii* were deposited at the CMI under the Nos. 287,750 and 287,751.

PRACTICE OF THE INVENTION

The disease causing material described herein may be applied to a region to be treated by being applied directly to the soil as pre-emergence treatment or as post-emergence treatment to plant foliage, or they can be mixed intimately with the soil. The preferred mode treatment is application after emergence of the plant foliage. The disease causing materials described herein may, for example, be applied to soil or to plant foliage in amounts of from about 100 g to 100 kg per hectare.

A herbicidal composition of this invention having any of the disease causing material described herein as its active ingredient may be formulated by mixing the material(s) with suitable inert carriers to obtain a composition generally used in agricultural compositions, such as a wettable powder, an emulsifiable concentrate, a granular formulation, a water soluble powder, an alginate, a xanthan gum and an aerosol. As solid carriers, bentonite, diatomaceous earth, apatite, gypsum, talc, pyrophyllite, vermiculite and clay may be used. A surface active agent may also be added, in order to give a homogeneous and stable formulation.

The disease causing material described herein can also be admixed with other active materials used in agronomic and horticultural management and which are compatible with it. Such active materials can be plant nutrients, fertilizers, insecticides, acaricides, fungicides, herbicides and nematocides.

The concentration of the disease causing materials in the mycoherbicidal composition of this invention may vary according to the type of formulation. Suitable concentrations are, for example, in the range of from about 5 to 80 weight percent, preferably from about 10 to 60 weight percent, in a wettable powder; and from about 5 to 70 weight percent, preferably from about 20 to 60 weight percent, in a granular formulation.

The material or materials employed in practice of this invention may be obtained by cultivation of the fungus in a suitable nutrient medium. The composition of the cultivation medium per se and the cultivation conditions form no part of this invention. Conventional cultivation media and cultivation conditions for these fungi are contemplated, surface cultivation using commercially available media, for example. The disease causing materials may be obtained by recovering of the non-dissolved material from the medium, for example, by centrifugation. This method produces a mixture of mycelium, sclerotia, etc. whose proportions may vary according to the age of the culture. The material is then converted, as desired, into a form suited to the intended application, into a wettable powder or emulsifiable concentrate, for example.

A wettable powder or an emulsifiable concentrate thus produced may be "diluted" with water to a specified concentration and used as a liquid suspension or a liquid emulsion for treating soils or plant foliage. Further, a granular formulation may be directly used for soil or foliage treatment.

PDA, oat meal agar and Czapek Dox Broth are sold by Difco Laboratories, Detroit, USA. V8 agar is made from V8 juice sold by many supermarkets.

Greenhouse experiments

Thistle plants grown in greenhouse at temperatures between 14° C. and 35° C. were infected when inoculated with a suspension of either pure mycelium, mycelium in combination with microsclerotia (Example 1) or in combination with pycnidia and conidia from *Phomopsis cirsii*.

The following Examples are hereinafter provided to illustrate detailed practice of the invention.

EXAMPLE 1

Young mycelium from 6–10 days old cultures of *Phomopsis cirsii* (CMI No. 287,569) or mycelium containing microsclerotia from up to 42 days old cultures of *Phomopsis cirsii*, grown in Roux flasks as surface culture on Czapek Dox Broth added 1.0 g of Difco bacto agar (Difco Laboratories) per liter medium, was rinsed under tap water to remove medium residues.

The mycelium was wiped off and blended with distilled water at high speed for two minutes in a Waring blender. The suspension was adjusted to contain 80 g of mycelium per liter suspension, using distilled water.

By means of a compressed air supplied spraying pistol (working pressure: 2 kg/cm$^2$) the inoculum was sprayed onto thistle plants, on different development stages, using enough volume to obtain runoff.

The plants were incubated for 24 hours in a dew chamber. Five to 7 days after inoculation, signs of infections appeared. Typically, it was black spots or stripes on the veins of the young leaves. The fungus invaded the stems systemicly from the leaves. After girdling of the stem, it grew downwards to the roots causing gradual dieback of the shoot.

A disease severity scale with 13 steps from immunity to complete death of the plant was worked out (see table I, below).

When *Phomopsis cirsii* infected at leaf basis, it normally took about 10 days from the first black spots were seen until the infected shoot died (perennial plants) or the entire plant died (annual plants).

When the infections occurred on more distal parts of the leaves, it took about 14 to 17 days to pass the same line of events.

*Phomopsis cirsii* was also able to invade the stem via involucral bracts of buds or flowering heads and thereby preventing further flowering of the plant.

The disease varied in severity between and within plant species (see table II and III, below, concerning the specificity of *Phomopsis cirsii*).

Table I

Disease Severity Scale

0: no symptoms (immune),
1: restricted leaf spots,
2: leaf spots in combination with some necrosis of leaf veins,
3: secondary veins necrotisized,
4: secondary and some mid veins necrotisized,
5: mid vein blackened until leaf basis,
6: death of entire leaf,
7: invasion of stem directly or via leaf veins,
8: necrotisation of stem cortex in longitudinal direction,
9: girdling of stem, heart rot in rosette,
10: necrotisation from girdling point towards basis of shoot,
11: death of shoot or entire plant dead (for annual and perennial plants, respectively),
12: dieback of new shoots,
13: entire plant dead (only for perennial plants).

EXAMPLE 2

Inoculation in the field with *Phomopsis cirsii* resulted in anthrocnose symptoms on *Cirsium arvense*. Abundant sporulation occured from solitary pycnidia scattered throughout bleached, straw-coloured patches in the extended black lesions on stems and sometimes on leaf veins. On stems of mature plants these lesions, which frequently developed from the leaf axils, were ranging in size from 1 to 15 cm, sometimes coalescing. Generally, it resulted in dieback of young and occasionally of mature plants.

EXAMPLE 3

Specificity test on *Phomopsis cirsii*

The same inoculation procedure and strain of *Phomopsis cirsii* as described in Example 1 was used to investigate the specificity of the fungus in the greenhouse on a collection of 147 different species selected from the following four groups: Wild plants (weeds and wild flora), agricultural plants, horticultural plants and plants for technical use.

Selection criteria for plant species were their relationship to *Cirsium arvense* and their occurence as crop or wild plants or as weeds.

18 plants from each species were inoculated in their 6th to 8th stage of foliation. As control, 6 plants from each species were sprayed with distilled water only.

The plants were finally incubated for 48 hours in a dew chamber.

The susceptibility of plants from the tribe Cardueae was evaluated one month after inoculation using the severity scale in Table I, above, ranging from 0 (immune) to 11 (death of the entire annual plant) or 13 (death of the entire perennial plant). The results appear from Table II, below.

TABLE II

| Cardueae Species | Disease Severity |
| --- | --- |
| Carduus acanthoides L. | 1–13 |
| Carduus crispus L. | 2–3 |
| Carduus crispus L. f. alba | 2–3 |
| Carduus pycnocephalus L. | 9–13 |
| Carduus thoermeri Weinm. | 5 |
| Cirsium arvense (L.) Scop. | 3–12 |
| Cirsium carlinoides Fisch. | 2–3 |
| Cirsium eriophorum (L.) Scop. | 6–13 |
| Cirsium vulgare (Savi.) Ten. | 2–3 |
| Cnicus benedictus L. | 9–13 |
| Cynara scolymus L. cv. Green globe | 2–6 |
| Galactites tomentosa (L.) Moensch. | 9–13 |
| Notobasis syriaca (L.) Cass. | 9–13 |
| Silybum marianum (L.) Gaertn. | 9–13 |
| Tyrimnus leucographus (L.) Cass. | 9–13 |

As seen from Table II, the plants from the tribe Cardueae were infected by the fungus. The only important crop plant, belonging to this group, which had a certain susceptibility towards Phomopsis cirsii is artichoke (Cynara scolymus). However, this susceptibility seems to be related to the crop variety.

Analogously, the susceptibility of plants not belonging to the tribe Cardueae was evaluated. The result of those tests was that all the plants tested were immune (0 on the severity scale in Table I, above). The group of plants and the number of species in each group of plants tested appears from Table III, below.

TABLE III

| Group of plants | Number of species tested |
| --- | --- |
| COMPOSITAE | |
| Tubuliflorae | |
| Heliantheae | 6 |
| Anthemideae | 9 |
| Astereae | 5 |
| Calenduleae | 1 |
| Helenieae | 1 |
| Inuleae | 2 |
| Senecioneae | 6 |
| Liguliflorae | 13 |
| CAMPANULACEAE | 1 |
| CANABACEAE | 1 |
| CHENOPODIACEAE | 5 |
| CONVOLVULACEAE | 1 |
| CRUCIFERAE | 22 |
| CUCURBITACEAE | 1 |
| DIPSACACEAE | 2 |
| EUPHORBIACEAE | 1 |
| GRAMINEAE | 9 |
| LILIACEAE | 1 |
| LINACEAE | 2 |
| PAPILIONACEAE (LEGUMINOSAE) | 18 |
| POLYGONACEAE | 1 |
| SOLANACEAE | 3 |
| UMBELLIFERAE | 2 |

EXAMPLE 4

Inoculation in the field with Septoria cirsii produced greyish necrotic leaf spots, ranging from about 0.3 to 1.0 cm in diameter. The spots were normally angular, but under humid conditions they became circular. Sporulation on the plant was never observed, but experiments showed that when dry infected leaves were incubated humid at about 5° C. for a couple of weeks, a few scattered pycnidia with abundant conidia were produced in the leaf spots.

EXAMPLE 5

Specificity test on Septoria cirsii

The pathogenicity of Septoria cirsii (CMI No. 287,751) was investigated by inoculating plants of Cirsium arvense with a suspension of conidia and crushed pycnidia (concentration: $10^6$ spores per ml), obtained from cultures grown on PDA plates. Distilled water was added to the plates and then the conidia and pycnidia were separated from the medium by gently scraping the medium surface.

Inoculations were carried out by means of a compressed air supplied spraying pistol (working pressure: 2 kg per $cm^2$). Each plant was sprayed until runoff.

The plants were incubated for 48 hours in a dew chamber.

The effects from the infection appear from table IV, below:

TABLE IV

| Days from infection | Symptoms |
| --- | --- |
| 5 | Minute necrotic spots surrounded by chlorosis (chlorotic halo). |
| 7 | Chlorosis coalescing. Necrosis grown to a diameter around 0.5 cm, distinct and angular. |
| 12 | All leaves, except the youngest, heavily chlorotisized. |
| 14–16 | Infected leaves wilted. |

With inoculum material produced and handled as described above, the specificity of Septoria cirsii was investigated in the greenhouse on a collection of 56 different plant species.

The susceptibility of the species was evaluated as occurrence of infections or no infections during a period of one month from the inoculation. Isolation of Septoria cirsii from the leaf spots confirmed the evaluations.

The results of the test on plants from the tribe Cardueae appear from table V, below, where "−" designates no signs of infection and "+" designates infection. As seen from the table, Septoria cirsii is specialised within the genus Cirsium, though infections were also found on Cynara scolymus and Notobasis syriaca. Centaurea macrocephala displayed typical symptoms, but Septoria cirsii could not be reisolated.

TABLE V

| Cardueae species | Infections |
| --- | --- |
| Arctium tomentosa Mill. | − |
| Carduus crispus L. f. alba | − |
| Carduus macrocephalus Desf. | − |
| Carduus nutans L. | − |
| Carduus pycnocephalus L. | − |
| Carduus squarosus (Ds.) Lowe. | − |
| Carduus tenuiflorus Curt. | − |
| Carthamus lanatus L. | − |
| Carthamus tinctorus L. | − |
| Centaurea cyanus L. | − |
| Centaurea jacea L. | − |
| Centaurea macrocephala Willd. | (+) |
| Cirsium acoule Scop. | − |
| Cirsium altissimum (L.) Spreng. | + |
| Cirsium andersonii Jeps. | − |
| Cirsium arvense (L.) Scop. | + |
| Cirsium flodmanii (Rydb.) Arthur | + |

TABLE V-continued

| Cardueae species | Infections |
| --- | --- |
| *Cirsium japonicum* DC. | + |
| *Cirsium oleraceum* (L.) Scop. | − |
| *Cirsium vulgare* (Savi.) Ten. | − |
| *Cnicus benedictus* L. | − |
| *Cynara cardunculus* L. (Cardoon) | − |
| *Cynara scolymus* L. cv. Grobe Van Loan | + |
| *Galactites tomentosa* (L.) Moensch. | − |
| *Notobasis syriaca* (L.) Cass. | + |
| *Onopordon algeriense* (Monby) Pomel | − |
| *Onopordon illyricum* L. | − |
| *Onopordon tauricum* Willd. | − |
| *Silybum marianum* (L.) Gaertn. | − |
| *Tyrimnus leucographus* (L.) Cass. | − |

Additionally, the susceptibility of plants not belonging to the tribe Cardueae was evaluated. No signs of infections were found on any of the plant species tested. The group of plants and the number of species in each group of plants tested appears from table VI, below.

TABLE VI

| Group of plants | Number of species tested |
| --- | --- |
| COMPOSITAE | |
| Tubuliflorae | |
| Heliantheae | 4 |
| Anthemideae | 2 |
| Helenieae | 1 |
| Inuleae | 2 |
| Senecioneae | 3 |
| Liguliflorae | 10 |
| CHENOPODIACEAE | 2 |
| PAPILIONACEAE (LECUMINOSAE) | 1 |
| UMBELLIFERAE | 1 |

Non-limiting examples of herbicidal compositions of this invention are illustrated below:

EXAMPLE 6

Wettable powder

| Components | Parts by weight |
| --- | --- |
| Disease causing material | 30 |
| White carbon | 30 |
| Diatomaceous earth | 32 |
| Sodium alkylsulfate | 8 |

These are mixed homogeneously and reduced to fine particles to provide a wettable powder. In use, it is diluted to a desired concentration with water, and is sprayed as a suspension.

EXAMPLE 7

Granular formulation

| Components | Parts by weight |
| --- | --- |
| Disease causing material | 7 |
| Talc | 38 |
| Bentonite | 10 |
| Clay | 38 |
| Sodium alkylsulfate | 7 |

These are mixed homogeneously and reduced to fine particles. The fine particles are made into granules, each having a diameter in the range of about 0.5–1.0 mm, to provide a granular formulation. In use it is directly applied.

I claim:

1. A method of controlling weeds which comprise treating a Compositae or Cardueae weed containing region with an effective amount of an inert carrier containing a disease causing material obtained by cultivation of the fungus *Phomopsis cirsii* or *Septoria cirsii*.

2. A method of controlling weeds, according to claim 1, further comprising applying a mycoherbicidal composition containing 10–60% of the disease causing material, balance being carrier.

3. A method according to claim 2 in which the composition is applied in an amount in the range from about 100 g to 100 kg per hectare.

4. A method according to claim 3 in which the weeds controlled are plants belonging to the Compositae.

5. A method according to claim 3 in which the weeds controlled are plants belonging to the Cardueae.

6. A method according to claim 3 in which the weeds are selected from the group consisting of: *Carduus acanthoides* L., *Carduus crispus* L., *Carduus crispus* L. f. alba, *Carduus pycnocephalus* L., *Carduus thoermeri* Weinm., *Cirsium arvense* (L.) Scop., *Cirsium carlinoides* Fisch., *Cirsium eriophorum* (L.) Scop., *Cirsium vulgare* (Savi.) Ten., *Cnicus benedictus* L., *Cynara scolymus* L. cv. Green globe, *Galactites tometosa* (L.) Moensch., *Notobasis syriaca* (L.) Cass., *Silybum marianum* (L.) Gaertn. and *Tyrimnus leucographus* (L.) Cass.

* * * * *